(12) United States Patent
MacAllister et al.

(10) Patent No.: US 11,779,588 B2
(45) Date of Patent: Oct. 10, 2023

(54) METHOD OF TREATING AMYOTROPHIC LATERAL SCLEROSIS

(71) Applicant: Woolsey Pharmaceuticals, Inc., St. Petersburg, FL (US)

(72) Inventors: Thomas MacAllister, Arlington, VA (US); Sven Jacobson, New York, NY (US)

(73) Assignee: Woolsey Pharmaceuticals, Inc., New York, NY (US)

( * ) Notice: Subject to any disclaimer, the term of this patent is extended or adjusted under 35 U.S.C. 154(b) by 88 days.

(21) Appl. No.: 17/502,507

(22) Filed: Oct. 15, 2021

(65) Prior Publication Data

US 2023/0120945 A1   Apr. 20, 2023

(51) Int. Cl.
| | |
|---|---|
| *A61K 31/551* | (2006.01) |
| *A61K 31/472* | (2006.01) |
| *A61K 31/4725* | (2006.01) |
| *A61P 25/28* | (2006.01) |
| *C07D 401/12* | (2006.01) |

(52) U.S. Cl.
CPC ............ *A61K 31/551* (2013.01); *A61P 25/28* (2018.01)

(58) Field of Classification Search
CPC ................ A61K 31/551; A61K 31/472; A61K 31/4725; A61P 25/28; C07D 401/12
See application file for complete search history.

(56) References Cited

U.S. PATENT DOCUMENTS

| | | | |
|---|---|---|---|
| 9,980,972 | B2 | 5/2018 | Lingor et al. |
| 2015/0031683 | A1 | 1/2015 | Lingor et al. |
| 2020/0155540 | A1 | 5/2020 | KC et al. |

OTHER PUBLICATIONS

International Search Report of International Application No. PCT/US21/55238; dated Jan. 26, 2022.
Patricia L. Andres et al., "Developing normalized strength scores for neuromuscular research", Muscle &Nerve, 2013, pp. 177-182, vol. 47.
I.S. Bakulin et al., "Structural and Functional Neuroimaging in Amyotrophic Lateral Sclerosis", Human Physiology, 2018, pp. 844-854, vol. 44.
BR Brooks, "El Escorial World Federation of Neurology criteria for the diagnosis of amyotrophic lateral sclerosis", Subcommittee on Motor Neuron Diseases/Amyotrophic Lateral Sclerosis of the World Federation of Neurology Research Group on Neuromuscular Diseases and the El Escorial "Clinical limits of amyotrophic lateral sclerosis", J Neurol Sci., Jul. 1994, pp. 96-107, vol. 124, Suppl.
BR Brooks et al, "El Escorial revisited: revised criteria for the diagnosis of amyotrophic lateral sclerosis", World Federation of Neurology Research Group on Motor Neuron Diseases, Amyotroph Lateral Scler Other Motor Neuron Disord, Dec. 2000, pp. 293-299, vol. 1, No. 5.
Jesse M. Cerdabaum et al., The ALSFRS-R: a revised ALS functional rating scale that incorporates assessments of respiratory function, BDNF ALS Study Group (Phase III), J Neurol Sci., Oct. 31, 1999 pp. 13-21, vol. 169.
Chen M. Liu et al, "Fasudil and its analogs: a new powerful weapon in the long war against central nervous system disorders?", Expert Opin Investig. Drugs, 2013, pp. 537-550, vol. 22.
Heather M. Clark et al., "Age and sex differences in orofacial strength", Dysphagia, Mar. 2012, pp. 2-9, vol. 27, No. 1.
Mamede De Carvalho et al., "Electrodiagnostic criteria for diagnosis of ALS", Clin Neurophysiol. Mar. 2008; pp. 497-503, vol. 119, No. 3.
Yangbo Feng et al., "Rho Kinase (ROCK) Inhibitors and Their Therapeutic Potential", J Med Chem., 2016, pp. 2269-2300, vol. 59, No. 6.
Adit U. Gurkar et al., "Identification of ROCK1 kinase a critical regulator of Beclin1-mediated autophagy during metabolic stress", Nat. Commun., 2013; 4:2189.
Mark E. Gurney et al., "Motor neuron degeneration in mice that express a humand Cu,Zn superoxide dismutase mutation", Science., 1994; pp. 1722-1725, vol. 264, No. 5166.
John Hodges et al., "The classification, genetics and neuropathology of frontotemporal dementia. Introduction to the special topic papers: part 1", Neurocase, 2001, pp. 31-35, vol. 7.
Y. Hou et al., "Changes in hippocampal synapses and learning-memory abilities in a streptozotocin-treated rat model and intervention by using fasudil hydrochloride", Neuroscience, 2012, pp. 120-129, vol. 200.
Mark Jacobs et al., "The structure of dimeric Rock I reveals the mechanism for ligand selectivity", J Biol Chem., 2006, pp. 260-268, vol. 281, No. 1.
Crispin Jenkinson et al., "Development and validation of a short measure of health status for individuals with amyotrophic lateral sclerosis/motor neurone disease: the ALSAQ-40", J. Neurol., 1999, pp. III16-III21, vol. 3.
Jan Koch et al., "Compassionate Use of the ROCK Inhibitor Fasudil in Three Patients with Amyotrophic Lateral Sclerosis", Frontiers in Neurology, 2020, Art. 173, pp. 1-8, vol. 11.
Paul Lingor et al., "ROCK-ALS, Protocol for a Randomized, Placebo-Controlled, Double-Blind Phase IIa Trial of Safety, Tolerability and Efficacy of the Rho Kinase (ROCK) Inhibitor Fasudil in Amyotrophic Lateral Sclerosis", Fronteirs in Neurology, 2019, Art. 293, pp. 1-11, vol. 10.
Paul Lingor et al., "Challenges and opportunities for Multi-National Investigator-Inidiated clinical trials for ALS: European and United States collaborations", Amyotrophic Lateral Sclerosis and Frontotemporal degeneration, 2021; pp. 419-425, vol. 22, No. 5-6.
P. Masrori et al., "Amyotropic lateral sclerosis: a clinical review" Eur J Neurology, 2020, pp. 1918-1929, vol. 27, No. 10.
Ricarda A. Menke et al., "Neuroimaging Endpoints in Amyotrophic Lateral Sclerosis", Neurotherapeutics, 2017, Jan, pp. 11-23, vol. 14, No. 1.

(Continued)

*Primary Examiner* — Brenda L Coleman
(74) *Attorney, Agent, or Firm* — MCBEE MOORE & VANIK IP, LLC; Susan McBee

(57) ABSTRACT

The present invention relates to the treatment of a sporadic ALS patient with oral fausdil at a dose of 180-240 mg/day. This results in an anticipated 25-50% reduction in the average decline over at least three months as measured using the revised ALS Functional Rating Scale.

16 Claims, No Drawings

(56) References Cited

OTHER PUBLICATIONS

Anroop B. Nair et al., "A Simple Practice Guide for Dose Conversion Between Animals and Human", J. Basic Clin Pharm., 2016, pp. 27-31, vol. 7, No. 2.
Osamu Nakagawa et al., "ROCK-I and ROCK-II, two isoforms of Rho-associated coiled-coil forming protein serine/threonine kinase in mice", FEBS Lett., Aug. 26, 1996, pp. 189-193, vol. 392, No. 2.
D. Neary et al., "Frontotemporal lobar degeneration. A 168 M. J. Strong et al. consensus on clinical diagnostic criteria", Neurology, 1998, pp. 1546-1554, vol. 51.
M. Shibuya et al., "Effect of Fasudil HCI, a protein kinase inhibitor, on cerebral vasospasm", Acta Neurochir, 2001, pp. 201-204, Suppl., vol. 77.
Michael Strong et al., "Amyotrophic lateral sclerosis—frontotemporal spectrum disorder (ALS-FTSD): Revised diagnostic criteria", Amyotrophic Lateral Sclerosis and Frontotemporal Degeneration, 2017, pp. 153-174, vol. 18.
Martin R. Turner et al., "Neuroimaging in amyotrophic lateral sclerosis", Biomarkers Med., 2012, pp. 319-337, vol. 6, No. 3.
Masayoshi Uehata et al., "Calcium sensitization of smooth muscle mediated by a Rho-associated protein kinase in hypertension", Nature, Oct. 3, 19970, pp. 990-994, vol. 389, No. 6654.
Hannelore K. Van Der Burgh . et al., "Multimodal longitudinal study of structural brain involvement in amyotrophic lateral sclerosis", Neurology, Jun. 2020, pp. e2592-e2604, vol. 94, No. 24.
Michael A. Vans Es et al., "Amyotrophic lateral sclerosis", Lancet, 2017, pp. 2084-2098, vol. 390, No. 10107.
Karen L. Wallace et al., "Development and validation of a self-report symptom inventory to assess the severity of oral-pharyngeal dysphagia", Gastroenterology, Apr. 2000, pp. 678-687, vol. 118, No. 4.
Hiroto Yamaguchi et al., "Structural basis for induced-fit binding of Rho-kinase to the inhibitor", J Biochem., Sep. 2006, pp. 305-311, vol. 140, No. 3.
"The Amyotrophic Lateral Sclerosis Functional Rating Scale (ALSFRS)", Georgetown University Hospital,—PMandR_ ALSRatingScale033111, 1998.
"Inhibition of Rho Kinase (ROCK) With Fasudil as Disease-modifying Treatment for ALS (ROCK-ALS)", ClinicalTrials.gov, Identifier: NCT03792490, 2020.

METHOD OF TREATING AMYOTROPHIC LATERAL SCLEROSIS

BACKGROUND OF THE INVENTION

Amyotrophic Lateral Sclerosis (ALS), commonly known as Lou Gehrig's disease, is a fatal neurodegenerative disease that affects motor neurons, resulting in a progressive loss of control of voluntary movements. It is associated with degeneration of upper motor neurons and their corticospinal axonal tracts (lateral sclerosis) and associated with the loss of lower motor neurons and their axons, which leads to muscle wasting (amyotrophy) and paralysis of voluntary muscles (Mitsumoto et al., 1998). Upper motor neurons originate in the motor region of the cerebral cortex or brain stem and move motor information underneath motor neurons that are directly responsible for stimulation of the target muscle. Their dysfunction causes stiffness due to continuous muscle contraction that interferes with walking, movement and speech. Lower motor neurons connect the brainstem and spinal cord to muscle fibers. Their dysfunction causes muscle atrophy, spasms small, local, involuntary muscle contraction. Many individuals with ALS die from respiratory failure within 48 months from the onset of symptoms and most within 3 to 5 years from onset.

ALS is thought to be caused by a combination of genetic factors, environmental factors, and aging-related dysfunction, similar to other neurodegenerative conditions. Apart from genetic factors, age and male sex increase the risk for ALS. Several studies have suggested environmental risk factors for ALS, such as smoking, body mass index, physical exercise, occupational and environmental exposures to metals, pesticides, β-methylamino-L-alanine, head injury, and viral infections. However, the causal relationship of these factors with ALS remains to be established (Masrori 2020).

About 90-96% of ALS cases are sporadic, with only 5-10% being familial due to inherited gene mutations.

ALS is also associated with protein inclusions in motor neurons and the CNS. Both sporadic and familial ALS are associated with abnormal accumulation TAR DNA-binding protein 43 (TDP-43) aggregates, which is thought to spread in a prion-like manner between cells. TDP-43 is the primary misfolded, mis-localized, ubiquitinated protein composing the major form of neuropathological aggregates in motor neurons in ALS. TDP-43 is a DNA/RNA binding protein that regulates RNA splicing and stability and microRNA. TDP-43 normally localizes to the nucleus where it functions in transcription, but misfolded TDP-43 aggregates in the cytosol, leading to a nuclear loss-of-function that might cause transcription deficits. It is unclear whether ALS pathogenesis is linked to loss of TDP-43 function or the pathology associated with the aggregates and cytoplasmic mis-localization.

Multiple molecular pathways have been implicated in the pathogenesis of ALS, such as failure of proteostasis, excitotoxicity, neuroinflammation, mitochondrial dysfunction and oxidative stress, oligodendrocyte dysfunction, cytoskeletal disturbances and axonal transport defects, disturbed RNA metabolism, nucleocytoplasmic transport deficits and impaired DNA repair. Interestingly, many of the genes associated with ALS appear to cluster in key pathways: protein quality control and degradation, RNA metabolism, and cytoskeletal and axonal transport (Masrori 2020).

Rho Kinase (ROCK) Inhibitors ALS. There are a number of publications addressing the use of rho kinase inhibitors in various animal models of neurodegeneration, including ALS. Most models are deficient in that they fail to reproduce the ALS (or other neurodegenerative disease) phenotype, or are pertinent only to familial ALS which is only 5-10% of ALS patients. As one example, U.S. Pat. No. 9,980,972 describes using fasudil in the SOD1 G93 mouse model, which harbors a mutation in the superoxide dismutase (SOD) protein. This patent claims treating familial, early-stage ALS with fasudil at 10-1200 ng/kg body weight per day or 1-12 mg/kg body weight per day. No humans were treated. Further, mutations in SOD are associated only with familial ALS which is why the claims are limited. The mice in the SOD model develop adult-onset neurodegeneration of spinal motor neurons and progressive motor deficits leading to paralysis. Further, the original SOD1-G93A mouse (originally described in Gurney et al., 1994) has since diverged into a family of strains with different genetic backgrounds and transgene expression levels, which significantly affect the onset and severity of symptoms. As one publication stated, "animal models have not been able to predict treatment response in humans, and there are no validated biomarkers for human ALS beyond the clinically supported diagnostic application of electromyography." (Menke 2016).

Another problem with the animal models is that many of them exhibit a high copy number of the mutant allele, i.e., they overexpress e.g., mutant SOD. This is vastly different from even human familial ALS, where afflicted patients have a mutation in one allele. Other models, such as TARDBP (TDP-43) mice that display TDP-43, also rely on overexpression approaches that do not replicate human ALS.

Fasudil was administered to three (3) human ALS patients on a compassionate use basis (Koch et al. 2020). One patient had familial ADS and the two other patients had probable ADS. Patients were dosed with 30 mg of intravenously administered fasudil twice daily over 20 consecutive working days (not weekends). There were no conclusive results beyond safety. Currently, there are clinical trials in progress in Germany, Switzerland and France for infusion of fasudil according to the same intravenous administration and dosing schedule. (Lingor et al., 2019). The trial is designed to treat three parallel groups: fausdil 15 mg twice daily, fasudil 30 mg twice daily, and matching placebo. No updates on this trial were available in September 2021 except for a publication detailing the unanticipated legal, administrative and financial complexities of a multi-national trial to which U.S.-based trials were proposed added but were not. (Lingor 2021).

Other publications disclose using unrealistic routes of administration (e.g., intraventricular injection) of fausdil for treatment of neurological and proteinopathy-associated diseases, and many do not use appropriate dosing. In this regard, standard formulas exist for converting doses used in animals to the same dose in humans. Human equivalent dose (HED) can be calculated, for example, using Table 1 of Nair & Jacob (2016), which are the same conversions used by the US FDA.

There exists a significant unmet need to provide new, therapies that show benefit in non-familial ALS in humans, not just animals with the genetic mutations that do not recapitulate most of the ALS population.

SUMMARY OF THE INVENTION

The invention contemplates the treatment of a sporadic ALS patient using fasudil.

In one embodiment, the patient has classic ALS. In a specific embodiment, the patient has only lower motor neuron involvement.

In another specific embodiment, the patient has only upper motor neuron involvement.

In one embodiment, the patient has ALS with frontotemporal dementia (ALS-FTD).

In another embodiment, oral fasudil is administered orally. In a specific embodiment, the fasudil is fasudil hydrochloride hemihydrate.

In one embodiment, fasudil is administered to the patient orally in a daily dose of between 180 and 240 mg per patient per day.

In another embodiment, fasudil is administered to the patient three times daily for a total of 240 mg/patient/per day.

In a further embodiment, fasudil is administered to the patient three times daily at 60 mg for a total of 180 mg/patient/day.

In another embodiment, the sporadic ALS patient treated has Tar DNA Binding Protein 43 (TDP-43) inclusions. In a specific embodiment, the pathological TDP-43 is due to a sporadic mutation in the TARDBP gene encoding TDP-43.

In a specific embodiment, the sporadic ALS patient is genetically male. In another embodiment, the sporadic ALS patient is genetically female.

In one embodiment, treatment of a sporadic ALS patient results in a greater-than fifty-percent reduced rate of decline on the revised ALS Functional Rating Scale (ALSFRS-R) as measured over six to twelve months.

In still another embodiment, treatment of a sporadic ALS patient results in a stabilization of the revised ALSFRS-R for at least 6 months.

In certain embodiments, treatment of a sporadic ALS patient results in a reduction in the rate of decline of at least one of the twelve domains of the ALSFRS.

In another embodiment, treatment of a sporadic ALS patient results in reduced muscle wasting and reduced paralysis of voluntary muscles.

Still other embodiments contemplate the treatment of an ALS patient with reduced slow vital capacity (SVC) as predicted by the patient's gender, age and the patient does not present with bulbar symptoms.

Certain embodiments involve the treatment of an ALS patient with an ALSFRS score of ≤36.

Some embodiments involve treating an ALS patient with fasudil hydrochloride, wherein the patient is also treated with riluzole and/or edaravone.

In another embodiment, an ALS patient is treated with fasudil hydrochloride, wherein the patient is also treated with taurursodiol and sodium phenylbutyrate.

DETAILED DESCRIPTION OF THE INVENTION

The invention is based on the discovery that orally-administered rho kinase inhibitors, including fasudil, can be used to sporadic ALS.

ROCK Inhibitors

The inventive methods contemplate the administration of a rho kinase (ROCK) inhibitor in the treatment of a disease or condition. Two mammalian ROCK homologs are known, ROCK1 (aka ROKβ, Rho-kinase β, or p160ROCK) and ROCK2 (aka ROKα) (Nakagawa 1996). In humans, the genes for both ROCK1 and ROCK2 are located on chromosome 18. The two ROCK isoforms share 64% identity in their primary amino acid sequence, whereas the homology in the kinase domain is even higher (92%) (Jacobs 2006; Yamaguchi 2006). Both ROCK isoforms are serine/threonine kinases and have a similar structure.

A large number of pharmacological ROCK inhibitors are known (Feng, LoGrasso, Defert, & Li, 2015). Isoquinoline derivatives are a preferred class of ROCK inhibitors. The isoquinoline derivative fasudil was the first small molecule ROCK inhibitor developed by Asahi Chemical Industry (Tokyo, Japan). The characteristic chemical structure of fasudil consists of an isoquinoline ring, connected via a sulphonyl group to a homopiperazine ring. Fasudil is a potent inhibitor of both ROCK isoforms. In vivo, fasudil is subjected to hepatic metabolism to its active metabolite hydroxyfasudil (aka, M3). Other examples of isoquinoline derived ROCK inhibitors include dimethylfasudil and ripasudil.

Other preferred ROCK inhibitors are based on based on 4-aminopyridine structures. These were first developed by Yoshitomi Pharmaceutical (Uehata et al., 1997) and are exemplified by Y-27632. Still other preferred ROCK inhibitors include indazole, pyrimidine, pyrrolopyridine, pyrazole, benzimidazole, benzothiazole, benzathiophene, benzamide, aminofurazane, quinazoline, and boron derivatives (Feng et al., 2015). Some exemplary ROCK inhibitors are shown below:

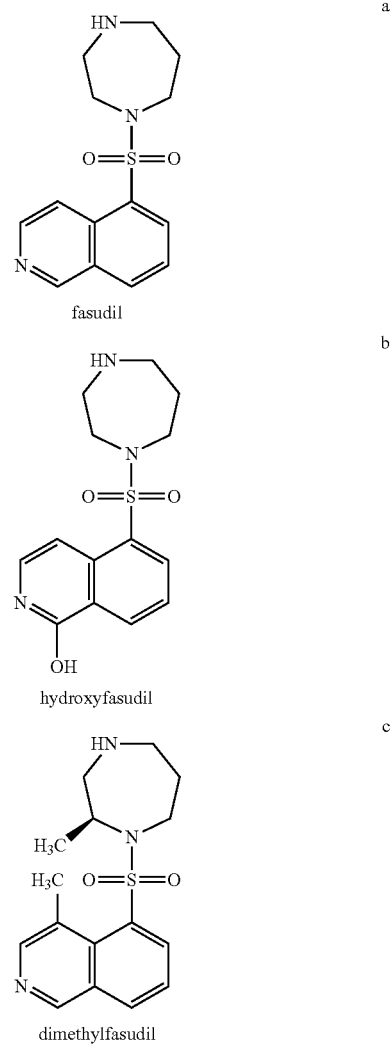

a
fasudil b
hydroxyfasudil c
dimethylfasudil

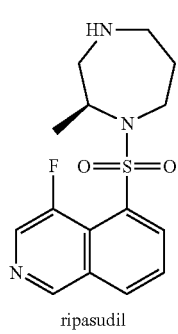

ripasudil

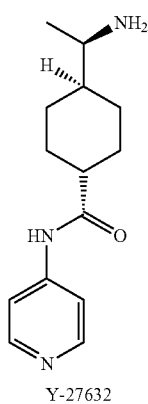

Y-27632

ROCK inhibitors according to the invention may have more selective activity for either ROCK1 or ROCK2 and will usually have varying levels of activity on PKA, PKG, PKC, and MLCK. Some ROCK inhibitors may be highly specific for ROCK1 or ROCK2 and have much lower activity against PKA, PKG, PKC, and MLCK.

A particularly preferred ROCK inhibitor is fasudil. Fasudil may exist as a free base or salt and may be in the form of a hydrate, such as a hemihydrate.

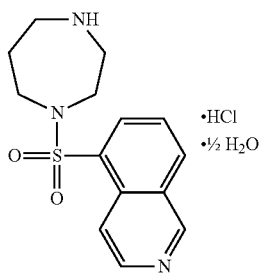 [SMILES: O=S(=O)(c1cccc2cnccc12)N1CCCNCC1 ; Cl]

Hexahydro-1-(5-isoquinolinesulfonyl)-1H-1,4-diazepine monohydrochloride hemihydrate Fasudil is a selective inhibitor of protein kinases, such as ROCK, PKC and MLCK and treatment results in a potent relaxation of vascular smooth muscle, resulting in enhanced blood flow (Shibuya 2001). A particularly important mediator of vasospasm, ROCK induces vasoconstriction by phosphorylating the myosin-binding subunit of myosin light chain (MLC) phosphatase, thus decreasing MLC phosphatase activity and enhancing vascular smooth muscle contraction. Moreover, there is evidence that fasudil increases endothelial nitric oxide synthase (eNOS) expression by stabilizing eNOS mRNA, which contributes to an increase in the level of the potent vasodilator nitric oxide (NO), thereby enhancing vasodilation (Chen 2013).

Fasudil has a short half-life of about 25 minutes, but it is substantially converted in vivo to its 1-hydroxy (M3) metabolite. M3 has similar effects to its fasudil parent molecule, with slightly enhanced activity and a half-life of about 8 hours (Shibuya 2001). Thus, M3 is likely responsible for the bulk of the in vivo pharmacological activity of the molecule. M3 exists as two tautomers, depicted below:

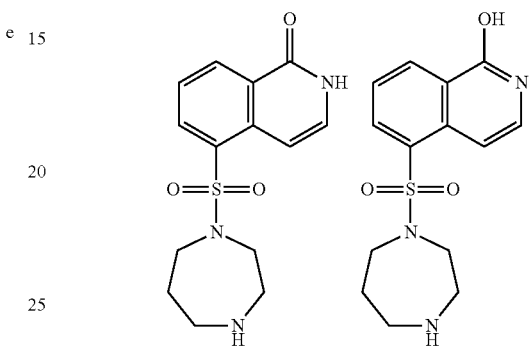

The ROCK inhibitors used in the invention, such as fasudil, include pharmaceutically acceptable salts and hydrates. Salts that may be formed via reaction with inorganic and organic acid. Those inorganic and organic acids are included as following: hydrochloric acid, hydrobromide acid, hydriodic acid, sulphuric acid, nitric acid, phosphoric acid, acetic acid, maleic acid, maleic acid, maleic acid, oxalic acid, oxalic acid, tartaric acid, malic acid, mandelic acid, trifluoroacetic acid, pantothenic acid, methane sulfonic acid, or para-toluenesulfonic acid.

TDP-43 and Other Abnormalities in ALS

TDP-43 is an essential DNA/RNA binding protein that is primarily located in the nucleus and is ubiquitously expressed. Deletion of the TARDBP (TDP-43-encoding gene) is lethal at the embryonic stage in mice.

TDP-43 is a primary component of ubiquitinated and hyper-phosphorylated cytosolic aggregates observed from post-mortem tissue of patients with ALS. Abnormal TDP-43 exists in about 97% of ALS patients, primarily in the motor neurons of the cerebral cortex but also in spinal cord. Over 50 mutations in the TARDBP are known. Generally, pathological TDP-43 in ALS is in a truncated form of either 25 or 35 kD. There is frequent mis-localization of TDP-43 from the nucleus to the cytoplasm in ALS, which could block cellular trafficking in the motor neurons.

ALS patients also exhibit mutation in proteins resulting in disruption of the ubiquitin-proteasome and autophagic clearance system which could result in the truncated TDP-43, improperly degraded. Despite the above, it is unclear whether TDP-43 contributes to ALS pathology or is a bystander of other defects, and targeting TDP-43 may be too late to prevent neurodegeneration, disease onset or progression.

Animal models of pathological TDP-43 that do not rely on artificial overexpression do not recapitulate hallmarks of ALS pathology. Motor deficits are subtle and occur in the later stages. This suggests that there are additional and unknown mechanisms contributing to ALS and that animal models of ALS, particularly where TDP-43 is overexpressed, bear little relevance to human disease etiology and/or progression.

ALS is also associated with mutations in genes encoding proteins involved in protein degradation and membrane degradation pathways, suggesting that an impairment of protein clearance is pathologic in ALS (and FTD). These include mutations in p62, valosin-containing protein (VCP), ubiquitin 2, and optineurin, which are all effectors of the autophagy and/or ubiquitin-proteasome system (UPS) protein degradation pathways. This suggestion is bolstered by the observations with C9orf72 insufficiency.

Another genetic defect associated with some sporadic and familial ALS patients is the presence of hexanucleotide repeat expansions (HRE) of GGGGCC in the non-coding region C9orf72 gene. Such HREs occur more than 30 times is associated with ALS, although most patients have hundreds or thousands of repeats. It is believed that the repeat expansion disrupts the C9orf72 protein function, resulting in haploinsufficiency (loss of function), but also lead to the pathological production of abnormal proteins. HRE in C9orf72 result in aborted RNA transcripts which then sequester RNA-binding proteins involved in transcription and splicing resulting in protein/RNA aggregates in the nuclei of the motor and frontal cortex neurons, hippocampus, cerebellum, and spinal cord.

Mutations in genes associated with familial ALS include single gene mutations in genes selected from C9orf72, SOD1, TARDBP, FUS and TANK-binding kinase 1 (TBK1). The present disclosure excludes familial (inherited) ALS due to those gene mutations.

Pharmaceutical Compositions

Pharmaceutical compositions of ROCK inhibitors usable in the are generally oral and may be in the form of tablets or capsules and may be immediate-release formulations or may be controlled- or extended-release formulations, which may contain pharmaceutically acceptable excipients, such as corn starch, mannitol, povidone, magnesium stearate, talc, cellulose, methylcellulose, carboxymethylcellulose and similar substances. A pharmaceutical composition comprising a ROCK inhibitor and/or a salt thereof may comprise one or more pharmaceutically acceptable excipients, which are known in the art. Formulations include oral films, orally disintegrating tablets, effervescent tablets and granules or beads that can be sprinkled on food or mixed with liquid as a slurry or poured directly into the mouth to be washed down.

Pharmaceutical compositions containing ROCK inhibitors, salts and hydrates thereof can be prepared by any method known in the art of pharmaceutics. In general, such preparatory methods include the steps of bringing a ROCK inhibitor or a pharmaceutically acceptable salt thereof into association with a carrier or excipient, and/or one or more other accessory ingredients, and then, if necessary and/or desirable, shaping, and/or packaging the product into a desired single- or multi-dose unit.

Pharmaceutical compositions can be prepared, packaged, and/or sold in bulk, as a single unit dose, and/or as a plurality of single unit doses. As used herein, a "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of the active ingredient, the pharmaceutically acceptable excipient, and/or any additional ingredients in a pharmaceutical composition of the invention will vary, depending upon the identity, size, and/or condition of the subject treated and further depending upon the route by which the composition is to be administered. The composition used in accordance with the methods of the present invention may comprise between 0.001% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

In certain embodiments, the pharmaceutical composition used in the methods of the present invention may comprise a diluent. Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

In certain embodiments, the pharmaceutical composition used in the methods of the present invention may comprise a granulating and/or dispersing agent. Exemplary granulating and/or dispersing agents include potato starch, corn starch, tapioca starch, sodium starch glycolate, clays, alginic acid, guar gum, citrus pulp, agar, bentonite, cellulose, and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (VEEGUM), sodium lauryl sulfate, quaternary ammonium compounds, and mixtures thereof.

In certain embodiments, the pharmaceutical composition used in the methods of the present invention may comprise a binding agent. Exemplary binding agents include starch (e.g., cornstarch and starch paste), gelatin, sugars (e.g., sucrose, glucose, dextrose, dextrin, molasses, lactose, lactitol, mannitol, etc.), natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (VEEGUM®), and larch arabogalactan), alginates, polyethylene oxide, polyethylene glycol, inorganic calcium salts, silicic acid, polymethacrylates, waxes, water, alcohol, and/or mixtures thereof.

In certain embodiments, the pharmaceutical composition used in the methods of the present invention may comprise a preservative. Exemplary preservatives include antioxidants, chelating agents, antimicrobial preservatives, antifungal preservatives, antiprotozoan preservatives, alcohol preservatives, acidic preservatives, and other preservatives. In certain embodiments, the preservative is an antioxidant. In other embodiments, the preservative is a chelating agent.

In certain embodiments, the pharmaceutical composition used in the methods of the present invention may comprise an antioxidant. Exemplary antioxidants include alpha tocopherol, ascorbic acid, ascorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

In certain embodiments, the pharmaceutical composition used in the methods of the present invention may comprise a chelating agent. Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

In certain embodiments, the pharmaceutical composition may comprise a buffering agent together with the ROCK inhibitor or the salt thereof. Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

In certain embodiments, the pharmaceutical composition used in the methods of the present invention may comprise a lubricating agent. Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

In other embodiments, the pharmaceutical composition of containing a ROCK inhibitor or salt thereof will be administered as a liquid dosage form. Liquid dosage forms for oral and parenteral administration include pharmaceutically acceptable emulsions, microemulsions, solutions, suspensions, syrups, and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates of the invention are mixed with solubilizing agents such as Cremophor™, alcohols, oils, modified oils, glycols, polysorbates, cyclodextrins, polymers, and mixtures thereof.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets, and pills, the dosage form may include a buffering agent.

Some compositions of the invention relate to extended- or controlled-release formulations. These may be, for example, diffusion-controlled products, dissolution-controlled products, erosion products, osmotic pump systems or ionic resin systems. Diffusion-controlled products comprise a water-insoluble polymer which controls the flow of water and the subsequent egress of dissolved drug from the dosage from. Dissolution-controlled products control the rate of dissolution of the drug by using a polymer that slowly solubilizes or by microencapsulation of the drug—using varying thicknesses to control release. Erosion products control release of drug by the erosion rate of a carrier matrix. Osmotic pump systems release a drug based on the constant inflow of water across a semi permeable membrane into a reservoir which contains an osmotic agent. Ion exchange resins can be used to bind drugs such that, when ingested, the release of drug is determined by the ionic environment within the gastrointestinal tract.

Methods of Diagnosis, Treatment, and Monitoring the Progression of ALS

The invention contemplates treating sporadic ALS with ROCK inhibitors. In one embodiment, the ROCK inhibitor is fasudil.

Diagnosis

Diagnosis of ALS can be done by clinical, electrophysiological and/or neuropathologic examination. In one embodiment, ALS diagnosis is made using El Escorial diagnostic criteria (Brooks 1994) successively updated in Airlie House and Awaji-shima criteria (de Carvalho 2008) (Brooks 2011). The Awaji criteria proposed two changes to the revised El Escorial. The first change was to use both electromyography and clinical data simultaneously to determine the presence of lower motor neuron (LMN) dysfunction. The second proposed change was to consider fasciculation potentials as evidence of ongoing denervation, equivalent in importance to fibrillation potentials.

In one embodiment, ALS diagnosis requires: (1) the presence of evidence of LMN degeneration by clinical, electrophysiological or neuropathological examination, (2) presence of upper motor neuron (UMN) degeneration by clinical examination, (3) presence of progressive spread of symptoms or signs within a region or other regions, as determined by history, clinical examination or electrophysiological tests, and (4) absence of electrophysiological or pathological evidence of other disease processes that might explain the observed clinical and electrophysiological signs.

Diagnostic categories include: definite ALS (clinical or electrophysiological evidence by the presence of LMN as well as UMN signs in the bulbar region and at least two spinal regions or the presence of LMN and UMN signs in three spinal regions), probable ALS (clinical or electrophysiological evidence by LMN and UMN signs in at least two regions with some UMN signs necessarily rostral to the LMN signs, and possible ALS (clinical or electrophysiological signs of UMN or LMN dysfunction in only one region or UMN signs alone in two or more regions or LMN rostral to UMN signs). The invention contemplates treating definite, probably and possible ALS.

Diagnostic criteria for ALS are summarized in Table 1 below:

TABLE 1

The diagnosis of ALS requires the presence of (positive criteria):
LMN signs (including EMG features in clinically unaffected muscles)
UMN signs
Progression of symptoms and signs
The diagnosis of ALS requires the absence of (diagnosis by exclusion):
Sensory signs
Sphincter disturbances
Visual disturbances
Autonomic features
Basal ganglion dysfunction
Alzheimer-type dementia
ALS 'mimic' syndromes [1]
The diagnosis of ALS is supported by:
Fasciculations in one or more regions
Neurogenic changes in EMG results
Normal motor and sensory nerve conduction
Absence of conduction block Clinical characteristics of the most common presentations of ALS, by designation and site of onset, are shown below in Table 2 (adapted from van Es 2017).

TABLE 2

| | Distribution | Clinical characteristics |
|---|---|---|
| | | Classic ALS (70%) [1] |
| Bulbar (33%) | Bulbar with involvement of other regions | Dysarthria is presenting feature; dysphagia usually develops later; generally both UMN and LMN signs<br>Bulbar UMN signs: exaggerated jaw jerk, pseudobulbar affect, and spasticity<br>Bulbar LMN signs: tongue wasting (never asymmetrical) and fasciculations |
| Spinal (66%) | Flail arm<br>Flail leg<br>Hemiplegic<br>Pseudo-polyneuritic | UMN involvement proximally in the arms, often with mild UMN signs in the legs<br>LMN involvement restricted to the legs, usually asymmetrical<br>Progressive, unilateral UMN involvement with facial sparing, sometimes with discrete LMN involvement<br>Predominantly distal LMN signs in the limbs with limited UMN involvement |
| | | ALS-FTD (5-15%) [2] |
| Bulbar or spinal | Distribution as in classic ALS | Classic ALS with a spinal or bulbar onset, but also signs of cognitive or behavioural changes, or both, fulfilling the diagnostic criteria for FTD. Patients most commonly have behavioural variant FTD with apathy and loss of sympathy as the commonly affected behavioural domains; semantic dementia is also seen. |
| | | Isolated bulbar involvement (5%) |
| Bulbar | Bulbar only | Bulbar signs that remain restricted to the bulbar region for an extended period of time (years) without spreading to other regions<br>Patients are predominantly women, have a spastic dysarthria, and commonly have emotional lability |
| | | Restricted phenotypes of ALS (10%) |
| | | Progressive spinal muscular atrophy (only LMN involvement) |
| Spinal | Spreading from a focal onset or patchy | Generalised LMN involvement; onset can be focal or patchy, but there is clear progression to other regions with time, eventually leading to respiratory failure<br>Average survival is longer than for classical ALS; patients should be followed regularly as UMN involvement can become apparent during the disease course |

TABLE 2-continued

| | Distribution | Clinical characteristics |
|---|---|---|
| | Primary lateral sclerosis (only UMN involvement) | |
| Bulbar or lower limbs | Spread from bulbar to limbs, from legs to arms and bulbar region; can be one-sided (Mill's syndrome) | Exclusive UMN signs for more than 4 years; UMN-predominant ALS, LMN signs can become evident with time; survival ranges from more than 10 years to normal life expectancy |
| | Rare phenotypes (3%) | |
| Cachexia | Develops into classic ALS | Unexplained weight loss may precede UMN or LMN signs, or both |
| Respiratory onset, diaphragm and neck flexors | Diaphragm and neck flexors | Weakness of diaphragm and neck flexors; associated with poor prognosis |

[1] Signs of UMN or LMN, or both, in multiple regions at presentation
[2] Patients who fulfil the diagnostic criteria for both ALS and FTD
ALS = amyotrophic lateral sclerosis;
FTD = frontotemporal dementia;
LMN = lower motor neuron;
UMN = upper motor neuron Classification according to ALS phenotype is mainly based on the relative UMN versus LMN involvement and the regional distribution of involvement.

Diagnosis can be achieved using clinical and electro-physiological assessments. Electro-physiological testing includes without limitation electromyography (EMG). Ultrasound of the muscles can detect fasciculations that can aid in the diagnosis of ALS. In some instances, a muscle biopsy, which involves taking a small sample of muscle under local anesthesia, is performed.

Imaging of the brain and spinal cord by techniques including MRI to rule out other disease but use to confirm ALS is less established due to the heterogeneity of ALS. Various imaging techniques are reviewed in Turner et al. 2012. The most sensitive and specific techniques to diagnose the disease are diffusion-tensor MRI, MR spectroscopy, PET, a combination of several neuroimaging methods, and neuroimaging with transcranial magnetic stimulation. Diffusion-tensor MRI and MR spectroscopy can be used to monitor and predict the disease course. (Bakulin 2019). Recently, one group reported MRI differences between ALS patients with C904f72 mutations and with impaired cognition. (van der Burgh et al., 2020).

Other conditions should be ruled out in an ALS diagnosis. Among the conditions that resemble ALS are some forms of muscular dystrophy, the neurologic conditions known as spinal-bulbar muscular atrophy, intraspinal tumor, the nerve-to-muscle transmission disorder known as myasthenia gravis.

Strong et al. 2017 also reported revised diagnostic criteria for diagnosing ALS associated with frontotemporal spectrum disorder (ALS-FTSD). These criteria, which incorporated clinical, electrophysiological, neuropsychological, genetic and neuropathological characteristics, recognized that ALS could exist as a pure motor syndrome but that it can coexist with a frontotemporal dementia (ALS-FTD) as defined by the Neary or Hodges criteria (Hodges 2001) (Neary 1998).

Other symptoms of the motor neuron degeneration may be socially disabling and/or affect the patient's quality of life include sialorrhoea (drooling, excessive salivation, thickened saliva), pseudobulbar emotional lability (pathological weeping, laughing, or yawning), cramps (especially at night), spasticity, depression and anxiety, insomnia (caused by depression, cramps, pain, and respiratory distress), constipation, and fatigue (of central and/or peripheral origin). Many patients report difficulties in effectively clearing bronchial secretions including tenacious sputum, and mucus accumulation is a negative prognostic factor.

Cognitive and behavioral changes are an intrinsic component of some forms of ALS. As mentioned above, 5-15% of patients with ALS also have frontotemporal dementia (FTD), and up to 50% of patients with ALS have cognitive or behavioral changes within the spectrum of FTD. Disease presentations with cognitive or behavioral changes that do not fulfil formal diagnostic criteria can be grouped into 1 of 3 categories: ALS with behavioral impairment; ALS with executive dysfunction; and ALS non-executive dysfunction. Apathy and loss of sympathy are the most common behavioral symptoms, while fluency, language, social cognition, and executive function are the cognitive domains that are most often affected (van Es 2017).

Treatment of Sporadic ALS Patients with Fasudil

In one embodiment, the patient to be treated with oral fasudil has sporadic ALS. In another embodiment, the sporadic ALS patient has TDP-43-associated ALS.

In a specific embodiment, the patient has classical ALS. In another specific embodiment, the patient has bulbar-onset ALS.

In one embodiment, the sporadic ALS patient does not have another proteinopathy-associated neurodegenerative disease.

In a further embodiment, the sporadic ALS patient treated with oral fasudil does not have frontotemporal dementia (FTD). In another embodiment the sporadic ALS patient has ALS-FTSD or ALS-FTD.

In one embodiment, the sporadic ALS patient treated with oral fasudil is genetically male.

In another embodiment, the sporadic ALS patient treated with oral fasudil is between the ages of 40-75. In a specific embodiment, the sporadic ALS patient treated with oral fasudil is between the ages of 50-65.

In further embodiment, the sporadic ALS patient treated with oral fasudil is between the ages of 20-39.

In one embodiment, the sporadic ALS patient treated with oral fasudil hydrochloride hemihydrate.

In accordance with the treatment methods of the present invention, a therapeutically effective amount of a ROCK inhibitor or a pharmaceutically acceptable salt thereof is administered to a sporadic ALS patient one or more times a day. The lowest therapeutically effective amount of fasudil, for example, is 90 mg per day, generally administered in 2 to 3 equal portions to obtain the full daily dose. The highest therapeutically effective dose may be determined empirically as the highest dose that remains effective in alleviating one or more ALS symptoms, but does not induce an unacceptable level or adverse events. Fasudil, for example, generally will not be administered in a daily dose exceeding 240 mg.

One preferred dosing regimen involves the treatment with 60 mg of fasudil hydrochloride hemihydrate three times per day using an oral immediate-release formulation, for a total daily dose of 180 mg. Other daily doses will range from 90 mg to 180 mg per day b.i.d. A further dosing regimen involves the treatment with 90 mg of fasudil hydrochloride hemihydrate only two times per day using an immediate-release formulation, for a total daily dose of 180 mg. In other embodiments, fasudil hydrochloride may be administered once a day using an immediate-release formulation at 180 mg or 240 mg. Above 240 mg per day, kidney effects of the drug are generally unacceptable. Based on ROCK inhibitory activity, one skilled in the art can readily extrapolate the provided dosing ranges for fasudil to other ROCK inhibitors.

Another embodiment involves the treatment with 90-240 mg of fasudil hydrochloride hemihydrate once per day in an extended release dosage form. Treatment with an extended release total daily dose of 180 mg fasudil hydrochloride hemihydrate is preferred. Generally an extended release dosage form will contain between 180 and 240 mg of fasudil hydrochloride hemihydrate.

Methods of administering compositions according to the invention would generally be continued for at least one day. Some preferred methods treat for up to 30 days or up to 60 days or even up to 90 days or even more. Treatment for more than 60 days is preferred and treatment for at least 6 months is particularly preferred. The precise duration of treatment will depend on the patient's condition and response to treatment. Most preferred methods contemplate that treatment begins after the onset or appearance of symptoms.

It will be appreciated that dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

Methods of administering compositions according to the invention would generally be continued for at least one day. Some preferred methods treat for up to 30 days or up to 60 days or even up to 90 days or even more. Treatment for more than 60 days is preferred and treatment for at least 6 months is particularly preferred. The precise duration of treatment will depend on the patient's condition and response to treatment.

Combination Therapy

In some embodiments, fasudil is administered combination with a second therapeutic agent that treats ALS or symptoms thereof. In some of such embodiments, the second therapeutic agent is selected from riluzole, edaravone, tetrabenazine, masitinib, tofersen, ravulizumab-wevz, mesenchymal stem cell (MSC)-neurotrophic factor (NTF) cells, AMX0035 (phenylbutyrate and taurursodiol), talampanel, tamoxifen, methylcobalamine, Aeol 10150.

In a specific embodiment, the sporadic ALS patient is administered fasudil in combination with riluzole or edaravone at about 50 to 100 mg day. In a specific embodiment, riluzole is administered 50 mg twice daily.

Other agents can be co-administered to treat symptoms of ALS or associated comorbidities, including respiratory function, eating, depression and anxiety, pain, dysarthria, dysphagia, sialorrhoea, insomnia, behavior or mood, and constipation can also be co-administered.

In another embodiment, fasudil can be co-administered with other agents that have been used to treat or mitigate symptoms of ALS. Such agents include antidepressants, benzodiazepines, amiltriptyline, dextromethorphan hydrobromide/quinidine sulfate, anti-inflammatories, muscle relaxants (baclofen, botulinum toxin), anticonvulsants (gabapentin, sodium valproate), anti-cholinergic drugs (glycopyrronium bromide), atorvastatin, lithium carbonate, avanier 07-ACR-123 (Zenvia®), SB-509, thalidomide, arimoclomol, olanzapine, memantine, tamoxifen, pioglitazone, creatine monohydrate, botulinum toxin type B, dronabinol, coenzyme Q10, escitalopram (Lexapro®), sodium phenylbutyrate, R(+) pramipexole dihydrochloride monohydrate, sodium valproate, cyclosporin, corticosteroids, and/or modafinil.

The second therapeutic agent is to be administered sequentially or simultaneously.

In one embodiment, the patient is administered fasudil in combination with tetrabenzaine. In a specific embodiment, the tetrabenzaine is administered in a dose from 12.5 to 100 mg/patient/day.

In another embodiment, the patient is administered fasudil in combination with an anti-inflammatory.

In a further embodiment, the patient is administered fasudil in combination with an agent that enhances proteasome activity. Such agents include proflavine pimozide, cyclosporin A, mifepristone, chlorpromazine, loperamide, dipyrimidole, methylbenzethonium, verapamil, ursolic acid, betulinic acid, rolipram, DPCPX, PD169316, PAP1, PA26, PA28, TCH-165, MK-886, and AM-404.

In another embodiment, the patient is administered fasudil in combination with an agent that enhances autophagy. In one embodiment, the autophagy enhancer is BRD5631, carbamazepine, rapamycin, trehalose, trifluoperazine niguldipine, metformin, lithium carbonate, sodium valproate, and ABT-737.

In a further embodiment the patient treated with fasudil is being treated for depression. In a specific embodiment, the patient is treated with an anti-depressant such as citalopram or escitalopram.

Assessing Progression of ALS Following Fasudil Treatment

Progression of ALS is assessed by measuring progressive clinical weakness using various methods. One assessment is the revised ALS Functional Rating Scale (ALSFRS-R), which is based on coarse disability measures driven by LMN dysfunction and remote from histopathological changes, is the standard measure of ALS disease progression (Cedarbaum 1999). The ALSFRS-R consists of 12 questions that total 48 points. Improvement in ALSFRS-R with fasudil can be measured in a change from baseline over time after treatment. ALSFRS-R can also be used to delay progression compared to untreated ALS patients. An ALS patient on average will show an approximately 1 point per month decline in the ALSFRS-R. Although some progress much more rapidly and some much more slowly, most patients will show 0.5-1.5 point per month loss. The 12 domains of the ALSFRS assess speech, salivation, swallowing, cutting food, dressing and hygiene, turning in bed, walking, climbing stairs, dyspnea, orthopnea and respiratory insufficiency.

Progression of muscle weakness can also include strength testing (muscles), peripheral nerve and muscle imaging with ultrasound and MRI to measure muscle atrophy, respiratory function assessment (pulmonary testing), and bulbar dysfunction testing (swallowing, tongue, lip and cheek strength).

Handheld dynamometry (HHD, also called quantitative myometry) is a commonly used methodology for assessment of muscle strength in ALS clinical trials. Electrophysiological assessments of muscles can also be used to measure disease progression. These include compound motor action potential (CMAP) and motor unit number estimates (MUNE, MUNIX) which are nerve conduction assessments used to quantify the numbers of motor units innervating an individual muscle. Isometric testing using e.g., Tufts Quantitative Neuromuscular Exam (TQNE) or the accurate test of limb isometric strength (ATLIS) can be used to measure upper and lower extremity muscles. (Andres 2013). ATLIS measures isometric strength in 12 muscle groups in the arms and legs. Electrical impedance myography (EIM) is also used to evaluate how electrical currents flow through muscle.

Bulbar dysfunction can be measured using the Iowa Oral Performance Instrument measurements of tongue, lip, and cheek strength (Clark and Soloman 2012). The Sydney Swallow Questionnaire may also be useful (Wallace et al. 2000).

For measures of respiratory muscle function and weakness (diaphragm, bulbar, and accessory muscles), forced vital capacity (FVC) is one of the most used measures in clinical trials. FVC measures the full extent of a breath capable by a patient by measuring the amount of air expelled from a breath in the first second. This can be measured using spirometry. Other measures of pulmonary function in ALS have also been studied, including maximal voluntary inspiratory or expiratory pressures. It is an indicator of disease progression in ALS patients. Slow vital capacity (SVC) is also often used which measures the normal slow breathing in and exhaling out of the patient.

Other lung measurements that can be used include the maximum mid-flow expiratory flow rate and peak cough flow. The latter involves coughing once the lungs have been emptied. Respiratory pressure meters can also assess respiratory strength to determining the maximum inspiratory pressure (MEP).

Many patients report difficulties in effectively clearing tenacious sputum, and mucus accumulation is a negative prognostic factor. Accordingly Weight loss is a predictor of shorter survival in amyotrophic lateral sclerosis (ALS).

Patients with older age, bulbar-onset, early respiratory dysfunction, and a lower score on the ALSFRS-R have a poorer prognosis.

Outcomes

In one embodiment, treatment of a sporadic ALS patient with fasudil reduces or reverses the progression ALS. Typically, this is measured using the ALSFRS-R and treatment with fasudil will slow the rate of decline in one or more of the twelve domains. The average rate of decline is one point per month, but it should be determined empirically over two to twelve months prior to fasudil treatment and then the effectiveness of fasudil treatment is determined by assessing progression over the same duration following starting fasudil treatment. Slowing or stopping the decline based on the ALSFRS is considered a successful treatment, as is reversing the decline.

In one embodiment, treatment of a sporadic ALS patient with fasudil reduces or reverses the loss of motor neuron demyelination or deterioration. Less deterioration can be measured by techniques including imaging, for example, diffusion-tensor MRI, MR spectroscopy, PET, neuroimaging with transcranial magnetic stimulation, or any combination thereof.

In another embodiment, treatment of a sporadic ALS patient with fasudil improves muscle deterioration (atrophy), reduces muscle paralysis or contraction, and reduces or prevents spreading of muscle fasciculations (twitches). In a specific embodiment, treatment of a sporadic ALS patient with fasudil reduces extremity muscle deficits. Muscle weakness can be evaluated using any method, e.g., strength testing, dynamometry (including hand-held), force transducers (strain gauges), electrophysiological assessments, isometric testing, and peripheral nerve and muscle imaging with ultrasound and MRI.

In a further embodiment, bulbar dysfunction is improved upon treatment of a sporadic ALS patient with fasudil as determined using e.g., the Iowa Oral Performance Instrument measurements of tongue, lip, and cheek strength or the Sydney Swallow Questionnaire. In a specific embodiment, fasudil treatment of a sporadic ALS patient improves swallowing and eating, reduces or delays progression of dysphagia, reduces slurred speech (dysarthria), and enables the ALS patient to retain a healthy weight. Assessments such as clinical MRI, needle EMG, the Frenchay Dysarthria Assessment, the Videofluoroscopic Swallowing Exam (VFSE), Maximum Tongue Pressure Test, and/or the EAT-10 screening tool, Improvements can also be assessed by speech pathologists and dieticians.

In another specific embodiment, treatment of a sporadic ALS patient with fasudil improves respiratory function. In a specific embodiment, fasudil treatment improves FVC %, oxygen saturation.

In another embodiment, treatment of a sporadic ALS patient reduces fatigues, improves poor balance and reduces tripping, improves grip.

In a further embodiment, the improvement is measured by improvements in the 48-point ALSFRS-R rating scale score, or any sub-scale thereof such as the activities of daily living (ADL) sub-score, relative to the score before being treated with fasudil hydrochloride. In another embodiment, the scale is the ALSAQ-40, which is a disease-specific questionnaire that was created specifically to assess health-related quality of life in patients with ALS. (Jenkinson et al., 1999). In a specific embodiment, improvement occurs with a higher score from baseline. In another embodiment, a consistent score over time without dropping is evidence of delayed progression of ALS.

In another embodiment, the improvement is measured by delayed reductions in the ALSFRS-R rating scale score relative to patients with sporadic ALS patient not being treated with fasudil.

In a further embodiment, treatment of a sporadic ALS patient with fasudil reduces motor neuroinflammation.

In another embodiment, the invention provides a method of reducing, reversing, or preventing the accumulation of TDP-43 in a sporadic ALS patient, the method comprising administering to said subject an effective amount of fasudil or a pharmaceutically acceptable salt thereof.

In another embodiment, TDP-43 cytoplasmic mis-localization is reduced upon treatment of a sporadic ALS patient with fasudil.

In embodiments, the TDP-43 aggregation, phosphorylation and/or ubiquitination is reduced by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100% upon treating a sporadic ALS patient with fasudil.

In other embodiments, fasudil treatment reduces or mitigates symptoms of ALS.

In one embodiment, treatment of a sporadic ALS patient improves survival (delays death). In one embodiment, survival is extended beyond the typical 2 years. In a further embodiment survival is extended beyond 2 years, beyond 3 years, beyond 4 years, and beyond 5 years. In another embodiment, survival is extended by 3 months to a year.

Patient Sub-Populations

Certain patient sub-populations, such as renally impaired patients and/or older patients (e.g., 65 or older) may need lower doses or extended release formulations instead of immediate release formulations. Fasudil hydrochloride hemihydrate may have higher steady-state concentrations when given at usual doses to patients with renal disease and lower doses to lower the Cmax or delay the time to Cmax (increase the Tmax) may be required.

Renal dysfunction occurs with age and as the result of numerous disorders, including liver cirrhosis, chronic kidney disease, acute kidney injury (for example, due to administering a contrast agent), diabetes (Type 1 or Type 2), autoimmune diseases (such as lupus and IgA nephropathy), genetic diseases (such as polycystic kidney disease), nephrotic syndrome, urinary tract problems (from conditions such as enlarged prostate, kidney stones and some cancers), heart attack, illegal drug use and drug abuse, ischemic kidney conditions, urinary tract problems, high blood pressure, glomerulonephritis, interstitial nephritis, vesicoureteral, pyelonephritis, sepsis. Kidney dysfunction may occur in other diseases and syndromes, including non-kidney-related diseases that may occur along with kidney dysfunction, for example pulmonary artery hypertension, heart failure, and cardiomyopathies, among others.

Kidney function is most often assessed using serum (and/or urine) creatinine. Creatinine is a breakdown product of creatine phosphate in muscle cells and it is produced at a constant rate. It is excreted by the kidneys unchanged, principally through glomerular filtration. Accordingly, elevated serum creatinine is a marker for kidney dysfunction and it is used to estimate glomerular filtration rate.

Normal levels of creatinine in the blood are approximately 0.6 to 1.2 mg/dL in adult males and 0.5 to 1.1 mg/dL in adult females. When creatinine levels exceed these figures, the subject has renal dysfunction, and is, therefore, treatable according to the invention. Mild renal impairment/dysfunction occurs in the range of 1.2 mg/dL to 1.5 mg/dL. Moderate renal impairment/dysfunction is considered to occur at creatinine levels exceeding 1.5 mg/dL. Severe renal impairment, which includes what is considered to be renal failure, is defined as a serum creatinine level of ≥2.0 mg/dL or the use of renal replacement therapy (such as dialysis). Treating subjects with mild, moderate and severe renal impairment is specifically contemplated.

Patient size is an important factor to consider when using creatinine-based estimates of renal function. The units of drug clearance are volume/time (mL/min), whereas the units of estimated GFR for chronic renal disease are volume/time/standard size (mL/min/1.73 $m^2$). Generally, doses may be adjusted down (e.g., 40-50 mg per day) for smaller patients and up for larger (e.g., 120 mg per day) for obese patients. A smaller male would be about 160 pounds or less. A smaller female patient would weigh about 130 pounds or less. Patients having a Body Mass Index of 30 and higher is considered obese.

In addition, older patients may need a lower dose at initiation, with a gradual increase to the recommended dose after days or weeks. In another embodiment, older patients may need lower doses, e.g., 90 mg/day, for the duration of treatment, with anticipated titration up to the 180 to 240 mg/day dose.

It will be appreciated that dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

Example 1: Treatment of Sporadic Als with Fasudil-a Phase 2A Open-Label PRELIMINARY SAFETY, EFFICACY, AND BIOMARKER STUDY OF FASUDIL HCl IN PATIENTS WITH ALS The aim of the study is to assess the preliminary safety, efficacy, and effect on biomarkers of oral Fasudil HCl hemihydrate 180 mg per day (60 mg tid) and 240 mg/day (80 mg tid) (immediate release tablets) for 24 weeks, in patients with ALS. Patients can maintain their current doses of riluzole or edaravone. Use of more than one of the following drug classes will be disallowed: long-acting nitrates, beta-blockers, or calcium channel blockers. (Note: subjects may be on one of the drug classes.)

The use of phenylbutyrate and/or tauroursodeoxycholic acid is strongly discouraged during the study, and may result in study or study treatment discontinuation The study will evaluate the effects of Fasudil on changes in the slope of decline in the Revised ALS Functional Rating Scale (ALSFRS-R), slow vital capacity (SVC) and hand-held dynamometry (HHD). Specifically, the study objectives are:

1. To evaluate the effect of Fasudil on plasma and cerebrospinal fluid (CSF) biomarkers of neurodegeneration and inflammation.
2. To evaluate the effect of Fasudil on plasma biomarkers of muscle loss.

3. To measure the CSF penetration of Fasudil and its major metabolite (M3) in patients with ALS.

Study Design

Approximately 20 subjects between the ages of 18 and 75 with possible, probable laboratory-supported, probable, or definite ALS, as defined by El Escorial Revised ALS diagnostic criteria are eligible for inclusion in the study, provided their ALSFRS-R is declining by an average of 0.5-1.5 points per 4 weeks at the time of Screening 1 (see Inclusion Criterion 3 for estimation methods). The study will enroll sufficient subjects such that approximately 20 subjects have an average ALSFRS-R decrease between Screening 1 and V3/D1 of 0.5-1.5 points per 4 weeks. Replacement of subjects not considered evaluable may be considered.

After consent, participants will undergo two screening evaluations, which will occur over the course of the 8 weeks prior to dosing with study drug. At Screening 1/V1 (8 weeks before start of dosing), ALS assessments of ALSFRS-R/SVC/HHD will be performed, as will safety assessments. Subjects who meet the pertinent inclusion/exclusion criteria will return for a second screening visit (Screening 2/V2) approximately 4 weeks later, and ALS and safety assessment will again be conducted. Subjects who meet the pertinent Screening 2 study entry criteria will be enrolled into the study.

On V3/Day 1, evaluations will be performed and dosing with study drug will begin. Dosing will be initiated at 180 mg/day; after at least 10 subjects have been enrolled and safely treated at 180 mg/day for 4 weeks, subsequent subjects may be enrolled at 240 mg/day. Study drug will be taken for 24 weeks.

Participants will have an in-person or telephone visit at Week 1 (V4) to assess for safety and drug compliance. Additional follow-up visits will occur at Weeks 4 (V5), 8 (V6), 12 (V7), 18 (V8) and 24 (V9), during which ALS assessments of ALSFRS-R/SVC/HHD will be performed. A final visit (V10) will be conducted at Week 25 (or 7±2 days after early termination) for post-treatment follow-up evaluations.

Plasma biomarker collection will occur between enrollment and commencement of treatment, and at Week 12 (V7) and Week 24 (V9). CSF biomarker collection will occur between enrollment and commencement of treatment, and at Week 24 (V9).

Laboratory safety assessments and adverse events will be collected at each study visit. Subjects/caregivers will be asked to maintain a log of study drug compliance, which will be reviewed at each visit.

To minimize patient burden, visits/study procedures may be performed outside of the clinic (e.g., at home or other sample collection site), and interviews may be performed by telephone and/or telemedicine as appropriate.

Duration. The maximum duration of the study is 33 weeks:
 4 weeks between Screening 1 and Screening 2, and
 4 weeks between Screening 2 and commencement of treatment, and
 24 weeks of treatment, and
 1 week until the final post-treatment follow-up visit.

Study Endpoints

Safety. Safety will be assessed by examining the incidence of AEs and SAEs, clinically significant abnormal physical and neurological examination findings, changes in vital signs, 12-lead ECG, and hematology, blood chemistry, liver function, and urine tests.

Efficacy. The following efficacy endpoints will be evaluated;
1. Change in the slope of decline of ALSFRS-R during treatment vs. pre-treatment.
2. Change in slope of decline in slow vital capacity (SVC) during treatment vs. pre-treatment.
3. Changes in slope of decline in HHD measurements during treatment vs. pre-treatment.

ALSFRS-R. The ALSFRS-R is a validated rating instrument for monitoring the progression of disability in patients with ALS and is utilized for monitoring functional change in ALS patients. The score assesses various 4 domains including: (i) bulbar function (speech, salivation, swallowing); (ii) fine motor task (handwriting, cutting food and handling utensils, with or without gastrostomy, dressing and hygiene); (iii) gross motor task (turning in bed, walking, climbing stairs); and (iv) respiratory function (dyspnea, orthopnea and respiratory insufficiency).

Each item within a domain is attributed a score of 0 (complete loss of function) to 4 (normal), yielding a maximum score of 48 when the function is preserved.

Evaluators performing ALSFRS-R must be certified by the Northeast Amyotrophic Lateral Sclerosis Consortium (NEALS). Use of alternative certifications must be approved in writing by the Sponsor. The ALSFRS-R should be performed by the same rater at each visit if feasible.

SVC. Respiratory function is a critical predictor of survival in amyotrophic lateral sclerosis (ALS). The vital capacity will be determined using the upright SVC method. The SVC will be measured using the study-approved portable spirometer, and assessments will be performed using a face mask. Three SVC trials are required for each testing session, however up to 5 trials may be performed if the variability between the highest and second highest SVC is 10% or greater for the first 3 trials. Only the 3 best trials are recorded on the electronic case report form (eCRF). The highest SVC recorded is utilized for eligibility. At least 3 measurable SVC trials must be completed to score SVC for all visits after screening. Predicted SVC values and percent-predicted SVC values will be calculated using the Quanjer Global Lung Initiative equations.

Evaluators performing the SVC must be certified by NEALS. Use of alternative certifications must be approved in writing by the Sponsor. The SVC should be performed by the same rater at each visit if feasible.

Muscle strength. Muscle strength will be assessed by hand-held dynamometer (HHD). A spring-loaded device that "breaks" at pre-set forces will be used to assess readings obtained by HHD throughout the study. Grip strength dynamometry for both hands will be acquired, and the mean force in kilograms will be calculated. Measures will be obtained from each hand in triplicate.

Evaluators performing HHD must be certified by NEALS. Use of alternative certifications must be approved in writing by the Sponsor. The HHD should be performed by the same rater at each visit if feasible.

Exploratory. Other endpoints that will be assessed are biomarkers as described below:
1. Changes in plasma biomarkers of neurodegeneration (e.g., neurofilament light chain [NfL] and phosphorylated neurofilament heavy subunit [pNfH]), inflammatory markers (e.g., IFN-γ, VCAM-1, ICAM-1, IL-1, IL-6, IL-17α, TNF-α and C1q), as well as markers of inflammation and neurodegeneration in neuronal and/ or astrocytic exosomes (e.g., IL-6, tau, protein kinase B [AKT] and phosphorylated-AKT [p-AKT]) from pre-treatment.
2. Changes in CSF biomarkers of axonal degeneration and/or apoptosis (e.g., tau and NfL), inflammation, and markers of drug target engagement (e.g., species of phosphorylated tau [p-tau], p-NfL PTEN and AKT/p-AKT) from pre-treatment.
3. Changes in plasma biomarkers of muscle loss (e.g., actin, myosin, myosin light chain, troponin, titin, myozenin, alpha-actinin, nebulin, cofilin 2, tropomyosin 2, creatine kinase, myoglobin, sarcospan, integrin alpha 7, agrin, laminin 211, collagen IV, collagen VI, and collagen fragments) from pre-treatment.
4. The ratio of CSF Fasudil/M3 metabolite concentration to plasma Fasudil/M3 metabolite concentration measured after 24 weeks of treatment.

CSF will be analyzed for biomarkers of neurodegeneration, which may include but are not limited to:
NfL
phosphorylated tau species (e.g., P-tau181, pS202, pS386, Thr245, Thr377, Ser409)
phosphorylated NfL species (e.g., Ser26 and Ser 57)
total tau fragment levels
other tau species
markers of inflammation (e.g., IFN-γ, VCAM-1, ICAM-1, IL-1, IL-6, IL-17α, TNF-α, C1q)
other markers of target engagement (e.g., PTEN and AKT/p-AKT)

Results

ALSFRS-R. It is anticipated that Fasudil treatment at 180 mg/day will result in about a 35-50% reduction in the average decline over at least three months as measured on the revised ALS Functional Rating Scale (ALSFRS-R).

In an embodiment, mitigate the decrease in ALSFRS-R from the average 0.5 to 1.5 (inclusive) points per 4 weeks (when using the change between the Screening 1 ALSFRS-R and the most recent ALSFRS-R measure that is at least 12 weeks prior to Screening 1). If no prior values are available, the rate of decline can be estimated as follows: (48-value at screening)/[estimated number of months between screening and ALS symptom onset (weakness and/or dysarthria, and/or dysphagia).

SVC. a reduction in the slope since the slope is correlated with disease progression. Looks like on the order of a 20-50% decline in the monthly rate. In another embodiment, the decline is less than the average 2.5-3.0% per month. In a specific embodiment, the rate of respiratory decline is slowed to an average of 1.5 percentage points per month.

Muscle strength. Hand-held dynamometry (HHD) is a measure of muscle strength and scores decrease as ALS progresses. It is expected that treatment with Fasudil will reduce the anticipated decline in muscle strength that occurs with ALS patients.

Biomarkers. It is anticipated that Fasudil treatment will reduce the presence of and/or levels of of biomarkers associated with neuronal and axonal degeneration, and reduce the amount of biomarkers associated with muscle loss by 25-50%. Alternatively, treatment with Fasudil is expected to reduce the presence of and/or levels of biomarkers associated with neuronal and axonal degeneration, and reduce the presence of biomarkers associated with muscle loss as compared to that reported for patients not administered Fasudil.

LIST OF REFERENCES

Andres P L, English R, Mendoza M, et al. Developing normalized strength scores for neuromuscular research. Muscle Nerve 2013; 47:177-182.
Bakulin, I. S. et al., Structural and Functional Neuroimaging in Amyotrophic Lateral Sclerosis. Human Physiology. 2018; 44: 844-854.
Brooks B R, El Escorial World Federation of Neurology criteria for the diagnosis of amyotrophic lateral sclerosis. Subcommittee on Motor Neuron Diseases/Amyotrophic Lateral Sclerosis of the World Federation of Neurology Research Group on Neuromuscular Diseases and the El Escorial "Clinical limits of amyotrophic lateral sclerosis" J Neurol Sci. 1994 July; 124 Suppl( )96-107.
Brooks B R, Miller R G, Swash M, Munsat T L, El Escorial revisited: revised criteria for the diagnosis of amyotrophic lateral sclerosis. World Federation of Neurology Research Group on Motor Neuron Diseases. Amyotroph Lateral Scler Other Motor Neuron Disord. 2000 December; 1(5): 293-9.
Cedarbaum J M, Stambler N, Malta E, Fuller C, Hilt D, Thurmond B, Nakanishi A The ALSFRS-R: a revised ALS functional rating scale that incorporates assessments of respiratory function. BDNF ALS Study Group (Phase III). J Neurol Sci. 1999 Oct. 31; 169(1-2):13-21.
Chen M, Liu A, Ouyang Y, Huang Y, Chao X, Pi R. 2013. Fasudil and its analogs: a new powerful weapon in the long war against central nervous system disorders? Expert Opin Investig Drugs. 22:537-50.
Clark H M, Solomon N P, Age and sex differences in orofacial strength. Dysphagia. 2012 March; 27(1):2-9.
de Carvalho M, Dengler R, Eisen A, England J D, Kaji R, Kimura J, Mills K, Mitsumoto H, Nodera H, Shefner J, Swash M, Electrodiagnostic criteria for diagnosis of ALS. Clin Neurophysiol. 2008 March; 119(3):497-503.
Feng Y, LoGrasso P, Defert O, Li R, Rho Kinase (ROCK) Inhibitors and Their Therapeutic Potential. J Med Chem. 2016; 59*6): 2269-2300.
Gurkar A. U. et al., Identification of ROCK1 kinase a critical regulator of Beclin1-mediated autophagy during metabolic stress. Nat. Commun. 2013; 4:2189.
Gurney M E et al., Motor neuron degeneration in mice that express a humand Cu,Zn superoxide dismutase mutation. Science. 1994; 264(5166): 1722-25.
Hodges J R, Miller B. The classification, genetics and neuropathology of frontotemporal dementia. Introduction to the special topic papers: part 1. Neurocase. 2001; 7:31-5.5.
Hou Y, Zhou L, Yang Q D, Du X P, Li M, Yuan M, Zhou Z W, Changes in hippocampal synapses and learning-memory abilities in a streptozotocin-treated rat model and intervention by using fasudil hydrochloride. Neuroscience. 2012; 200: 120-129.
Jacobs M, Hayakawa K, Swenson L, Bellon S, Fleming M, Taslimi P, Doran J, The structure of dimeric ROCK I reveals the mechanism for ligand selectivity. J Biol Chem. 2006; 281(1): 260-68.
Jenkinson C et al., Development and validation of a short measure of health status for individuals with amyotrophic lateral sclerosis/motor neurone disease: the ALSAQ-40. J. Neurol. 1999; 3: III16-11121.
Koch, Jan C. et al., Compassionate Use of the ROCK Inhibitor Fasudil in Three Patients with Amyotrophic Lateral Sclerosis. Frontiers in Neurology. 2020; 11; Art. 173:1-8.

Lingor, Paul et. al., ROCK-ALS, Protocol for a Randomized, Placebo-Controlled, Double-Blind Phase Ha Trial of Safety, Tolerability and Efficacy of the Rho Kinase (ROCK) Inhibitor Fausdil in Amyotrophic Lateral Sclerosis. Fronteirs in Neurology. 2019; 10, Art. 293: 1-11.

Lingor, Paul et al., Challenges and opportunities for Multi-National Investigator-Inidiated clinical trials for ALS: European and United States collaborations. Amyotrophic Lateral Sclerosis and Frontotemporal degeneration. 2021; 22(5-6): 419-25.

Masrori and Van Damme, Amyotropic lateral sclerosis: a clinical review. Eur J Neurology. 2020; 27(10): 1918-29.

Menke Ricarda A, Neuroimaging Endpoints in Amyotrophic Lateral Sclerosis. Neurotherapeutics. 2017 January; 14(1): 11-23.

Nair A B and Jacob S, A Simple Practice Guide for Dose Conversion Between Animals and Human. J. Basic Clin Pharm. 2016; 7(2): 27-31.

Nakagawa O, Fukisawa K, Ishizaki T, Saito Y, Nakao K, Narumiya S, ROCK-I and ROCK-II, two isoforms of Rho-associated coiled-coil forming protein serine/threonine kinase in mice. FEBS Lett. 1996 Aug. 26; 392(2): 189-93.

Neary D, Snowden J S, Gustafson L, Passant U, Stuss D, Black S, et al. Frontotemporal lobar degeneration. A 168 M. J. Strong et al. consensus on clinical diagnostic criteria. Neurology. 1998; 51:1546-54

Shibuya M, Asano T, Sasaki Y. 2001. Effect of Fasudil HCl, a protein kinase inhibitor, on cerebral vasospasm. Acta Neurochir Suppl. 77:201-4.

Strong, Michael J. et al., Amyotrophic lateral sclerosis-frontotemporal spectrum disorder (ALS-FTSD): Revised diagnostic criteria. Amyotrophic Lateral Sclerosis and Frontotemporal Degeneration. 2017; 18: 153-174.

Turner, Martin R et al. Neuroimaging in amyotrophic lateral sclerosis. Biomark Med. 2012; 6(3) 319-37.

Uehata M, Ishizaki T, Satoh H, Ono T, Kawahara T, Morishita T, Tamakawa H, Yamagami K, Maekawa M, Narumiya S, Calcium sensitization of smooth muscle mediated by a Rho-associated protein kinase in hypertension. Nature. 1997 Oct. 30; 389(6654):990-4.

Van der Burgh, H. K. et al., Multimodal longitudinal study of structural brain involvement in amyotrophic lateral sclerosis. Neurology June 2020, 94 (24) e2592-e2604; DOI: 10.1212/WNL.0000000000009498.

van Es, M. A., Amyotrophic lateral sclerosis. Lancet. 2017; 390(10107): 2084-98.

Wallace K L, Middleton S, Cook I J. Development and validation of a self-report symptom inventory to assess the severity of oral-pharyngeal dysphagia. Gastroenterology. 2000 April; 118(4):678-87.

Yamaguchi H, Miwa Y, Kasa M, Kitano K, Amano M, Kaibuchi K, Hakoshima T, Structural basis for induced-fit binding of Rho-kinase to the inhibitor Y-27632. J Biochem. 2006 September; 140(3):305-11.

The disclosure of each reference set forth herein is incorporated herein by reference in its entirety.

The invention claimed is:

1. A method of treating a patient with sporadic amyotrophic lateral sclerosis (ALS), comprising orally administering a therapeutically effective amount of a fasudil or hydroxyfasudil (M3), or a pharmaceutically acceptable salt thereof, to the patient.

2. The method according to claim 1 wherein the patient has classic ALS.

3. The method according to claim 1, wherein the patient has ALS with frontotemporal dementia (ALS-FTD).

4. The method according to claim 1, wherein the treatment results in 50% reduction in decline over at least three months as measured on the revised ALS Functional Rating Scale (ALSFRS-R).

5. The method according to claim 1, wherein the treatment results in reduced muscle wasting and reduced paralysis of voluntary muscles.

6. The method according to claim 1, wherein fasudil or a pharmaceutically acceptable salt thereof is administered.

7. The method according to claim 1, wherein the patient is treated with fasudil hydrochloride.

8. The method according to claim 1 wherein M3 is administered.

9. A method according to claim 1 where the patient is treated with a daily dose of 90 to 240 mg/day.

10. The method according to claim 9, wherein the daily dose is 180 mg/day.

11. The method according to claim 9, wherein the daily dose is 240 mg/day.

12. The method according to claim 9, wherein the dose is administered in three equal portions throughout the day.

13. The method according to claim 10, wherein the dose is administered in two equal portions throughout the day.

14. The method according to claim 10, wherein the fasudil is administered in a sustained release formulation.

15. The method according to claim 1, wherein the sporadic ALS patient is genetically male.

16. The method according to claim 1, wherein the sporadic ALS patient is genetically female.

* * * * *

UNITED STATES PATENT AND TRADEMARK OFFICE
CERTIFICATE OF CORRECTION

| | | |
|---|---|---|
| PATENT NO. | : 11,779,588 B2 | Page 1 of 1 |
| APPLICATION NO. | : 17/502507 | |
| DATED | : October 10, 2023 | |
| INVENTOR(S) | : Thomas MacAllister and Sven Jacobson | |

It is certified that error appears in the above-identified patent and that said Letters Patent is hereby corrected as shown below:

In the Claims

At Column 26, Line 12, in Claim 1, please delete:
"-tering a therapeutically effective amount of a fasudil or"
And insert:
-- -tering a therapeutically effective amount of fasudil or --

Signed and Sealed this
Seventh Day of November, 2023

Katherine Kelly Vidal
*Director of the United States Patent and Trademark Office*